United States Patent [19]

Lloyd et al.

[11] 4,452,845

[45] Jun. 5, 1984

[54] MOISTURE VAPOR TRANSMITTING FILM OF POLYURETHANE BLENDED WITH AN INCOMPATIBLE POLYMER

[75] Inventors: Ronald Lloyd, Sawbridgeworth; Peter J. Metcalfe, Stansted Mountfitchet, both of England

[73] Assignee: Smith and Nephew Associated Companies Limited, England

[21] Appl. No.: 512,961

[22] Filed: Jul. 12, 1983

Related U.S. Application Data

[63] Continuation of Ser. No. 292,214, Aug. 12, 1981, abandoned.

[30] Foreign Application Priority Data

Aug. 13, 1980 [GB] United Kingdom ............... 8026366

[51] Int. Cl.$^3$ .................... B32B 3/26; B32B 27/40
[52] U.S. Cl. .................... 428/220; 128/156; 428/315.7; 428/317.3; 428/317.7; 428/338; 428/343
[58] Field of Search ............ 128/156; 264/288.4, 264/288.8, 41, 49; 428/220, 315.5, 315.7, 315.9, 317.9, 317.3, 317.7, 338, 910, 343; 604/897, 370

[56] References Cited

U.S. PATENT DOCUMENTS

| | | | |
|---|---|---|---|
| 3,426,754 | 2/1969 | Bierenbaum | 128/156 |
| 3,536,638 | 10/1970 | Dosmann | 521/75 |
| 3,646,178 | 2/1972 | Traübel et al. | 525/130 |
| 3,844,865 | 10/1974 | Elton et al. | 428/330 |
| 3,870,593 | 3/1975 | Elton et al. | 428/315.5 |
| 3,932,682 | 1/1976 | Loft et al. | 428/315.5 |
| 3,975,316 | 8/1976 | Villa | 525/130 |
| 3,993,618 | 11/1976 | Muck et al. | 525/130 |
| 4,133,310 | 1/1979 | Lloyd et al. | 428/136 |

FOREIGN PATENT DOCUMENTS 1476791 6/1977 United Kingdom .

*Primary Examiner*—William J. Van Balen
*Attorney, Agent, or Firm*—Jacobs & Jacobs

[57] ABSTRACT

A moisture vapor transmitting film comprising a blend of polyurethane and an incompatible polymer characterized in that the incompatible polymer forms a discrete phase within a continuous matrix of polyurethane and that said film contains voids and processes for the manufacture thereof.

32 Claims, No Drawings

MOISTURE VAPOR TRANSMITTING FILM OF POLYURETHANE BLENDED WITH AN INCOMPATIBLE POLYMER

CROSS REFERENCE

This is a continuation of Ser. No. 292,214 filed Aug. 12, 981, now abandoned.

The present invention is concerned with moisture vapour transmitting polymer blend films, methods of manufacture and their use.

Moisture vapour transmitting polyurethane films are known and their use as backings in adhesive dressings is disclosed in British Patent Specification No. 1,280,361. This patent discloses that suitable polyurethane films are 25 microns thick and can have a moisture vapour transmission rate of approximately 1600 g/m²/24 hours at 37° C. at 100% to 10% relative humidity difference.

Such thin polyurethane films are very flexible and conformable to skin but are difficult to handle especially when coated with adhesive. Polyurethane films of suitable thickness to enable them to be handled have much lower moisture vapour transmission rates. A method of making porous polyurethane films by permanently stretching thermoformed polyurethane films containing large amounts of inorganic filler is disclosed in U.S. Pat. Nos. 3,844,865 and 3,870,593. However it is also disclosed in the U.S. patents that the porous films have physical properties similar to paper and that water and aqueous solutions can permeate these films. British Patent Specification No. 1,226,841 discloses porous films of a blend of polyurethane and polyvinyl chloride.

It would be advantageous to have a moisture vapour transmitting polyurethane film of a handleable thickness which is impermeable to liquid water and capable of being a barrier to bacteria in bandages and dressings.

Elastomeric moisture vapour transmitting polyurethane blend film suitable for bandages and dressings have now been discovered which are impermeable to liquid water.

The present invention provides a moisture vapour transmitting elastomeric films comprising a blend of polyurethane and an incompatible polymer characterised in that the incompatible polymer forms a discrete particulate phase within a continuous matrix of polyurethane and that said film contains voids.

The term "voids" when used herein means small holes within the film. These small holes may interrupt the surface or may coalesce. The voids normally have a diameter from 2 to 12 microns, for example 3 to 6 microns. Voided films of this invention are impermeable to liquid water and therefor do not contain openings or passages which provide a continuous pathway through the film.

In a second aspect this invention provides a moisture vapour transmitting elastomeric film comprising a blend of polyurethane and a discrete particulate phase characterized in that the discrete particulate phase comprises an incompatible polymer and that said film contains voids.

Suitable polyurethanes for use in this invention are those which can be formed into an elastomeric film.

Especially suitable are the class of polyurethanes which are known as thermoplastic polyurethanes. Aptly the polyurethane employed is a linear polyester or polyether polyurethane. Preferred are linear thermoplastic polyurethanes known as Estanes (Trade Mark) made by B. F. Goodrich and Co. Ltd., which are a range of linear olyester and polyester urethanes. A preferred polyurethane of this type is Estane 580201 which is an extrusion grade linear polyether urethane.

Other suitable linear thermoplastic polyurethanes include Estane 5714, Pellethane 2103-8AE (Trade Mark) available from Upjohn and Elastollan L85-A10 and P85-M10 (Trade Marks) available from Elastogran (U.K.) Limited.

The polyurethane can contain additives such as fillers and antioxidants.

It is preferred that the particles of the discrete particulate phase of incompatible polymer should be spherical or ellipsoidal in shape and have a diameter of at least 1 micron, for example 2 microns to 5 microns.

Suitable incompatible polymers include those derived from polymerisation of vinyl hydrocarbons, for example polyethylene and polystyrene.

It is desirable that mechanical and physical properties of the incompatible polymer are significantly different from that of the polyurethane at temperatures at which the film will cold draw.

It is particularly desirable that the incompatible polymer should have a higher modulus than that of the polyurethane at the cold draw temperatures.

It is also desirable that the incompatible polymer has a lower melt viscosity than the polyurethane at its melt forming temperature.

In this respect it is often advantageous for the incompatible polymer to contain a filler such as a reinforcing filler. It follows that certain preferred films of this invention include these in which the incompatible polymer contains a filler such as an inorganic filler. Such fillers are frequently present by 4 to 15%, for example 10 to 12%. A particularly apt filler is calcium carbonate.

An especially suitable incompatible polymer is low density polyethylene containing a filler.

Another especially suitable incompatible polymer is polystyrene. The polystrene may be an unmodified (homopolymer) or rubber modified grade. High impact polystyrene is a preferred incompatible polymer.

The incompatible polymer can advantageously contain a lubricant. Suitable lubricants include fatty acids and their amide and ester derivatives, such as stearamide and glyceryl monostearate. Suitably the lubricant may be present in amounts up to 10% by weight but preferably in amounts not more than 5% by weight of the incompatible polymer. A favoured low density polyethylene contains 5% by weight of stearamide.

A preferred low density polyethylene is a purging composition reference DG 0964 supplied by British Petroleum. The composition consists essentially of a low density polyethylene containing about 11% parts by weight of a filler consisting mainly of silica with small amounts of calcium carbonate and small amounts of glyceryl monostearate, stearamide and a phenolic antioxidant.

A preferred polystyrene is a high impact polystyrene reference 6MW supplied by R. H. Cole Ltd.

The proportions of polyurethane and the incompatible polymer in the blend depend on some extent on the individual polymers. However in general suitable blends contain 40% to 90% by weight, desirably 45% to 85% by weight and preferably 50% to 80% by weight of polyurethane.

One preferred blend contains 60% of a polyurethane (for example 60% by weight of Estane 58201) and 40% by weight of incompatible polymer for example low density polyethylene purging compound from British Petroleum. Another preferred blend contains 80% by weight of polyurethane (for example Estane 58201) and 20% by weight of high impact grade polystyrene reference 6MW from R. H. Cole Ltd. A further preferred blend contains 60% by weight of polyurethane and 40% by weight of high impact polystyrene.

The film of the invention can be used as a backing film for medical dressings and bandages such as adhesive coated first aid dressings and compression bandages. For these uses it is preferred that the film has a moisture vapour transmission rate of at least 200 g/m$^2$ more suitably at least 350 g/m$^2$, preferably at least 500 g/m$^2$ and most preferably at least 1000 g/m$^2$ at 100% −10% relative humidity difference.

Most aptly the film of this invention is used as the backing in an adhesive dressing such as a first aid dressing. Such dressings form a part of this invention.

It is preferred that adhesive coated medical dressings have a moisture vapour transmission rate of at least 150 g/m$^2$, suitably at least 250 g/m$^2$ and preferably at least 500 g/m$^2$ at 37° C. at 100% −10% relative humidity difference.

The adhesive coating layer can be discontinuous for example in the form of porous (including microporous) or pattern coated layers. However it is preferred that the adhesive coating layer is continuous.

Suitable continuous adhesive layers can comprise an acrylate ester copolymer or a polyvinyl ether. Preferred acrylate ester copolymer adhesives are disclosed in United Kingdom Application No. 8,106,707. A favoured acrylate ester copolymer of 47 parts by weight of 2-ethylhexyl acrylate, 47 parts by weight of n-butyl acrylate and 6 parts by weight of acrylic acid.

Suitably the thickness of the adhesive layer of adhesive dressings of the invention can be from 12.5 microns to 75 microns. Suitable thicknesses of the film backings of adhesive dressings of the invention are described hereinafter in relation to films of the invention.

The dressings of this invention will normally contain a pad covered with a non-adherent wound facing layer as is conventional in dressings of this type.

The moisture vapour transmission rate may be measured by the Payne Cup method. The method uses a cup 1.5 cm deep with a flanged top. The inner diameter of the flange is such to provide an area for moisture vapour transmission of 10 cm$^2$. In this method 10 ml. of distilled water is added to the cup and a sample of the material undert test, large enough to completely cover the flange, is clamped over the cup. The complete assembly is then weighed and placed in a cabinet where the temperature and relative humidity are maintained at 37° C. and 10% respectively. After 17 hours the cup is removed from the cabinet and allowed to cool at room temperature. After re-weighing, the mass of water lost by vapour transmission is calculated and the result expressed as in g/m$^2$/24 hrs. at 37° C. at 100% 1 10% relative humidity difference.

It is suitable that the film of this invention has a thickness of 0.0125 mm to 0.25 mm more suitable 0.05 mm to 0.25 mm, desirably 0.0125 mm to 0.125 mm and preferably 0.075 mm to 0.125 mm.

It is desirable that the film of this invention has a recoverable elastic strain of at least 100%, more suitably at least 150% and preferably at least 200%.

The film of the invention is normally opaque due to the voids in the body of the film.

The films of the invention have a soft surface feel when they are used in the manufacture of body contact articles.

The invention provides a process for making a film of this invention which comprises forming a film from a blend of polyurethane and an incompatible polymer and cold drawing (that is stretching at 10° to 45° C.) the film until voiding occurs and thereafter allowing the drawn film to contract.

It is preferred that the film is formed by hot melt process in particular by hot melt extrusion. It is also preferred that the blending of the polyurethane and the incompatible polymer is carried out under hot melt conditions although pre-mixing of the granules can be carried out by tumbling at room temperature.

FIG. 1 illustrates a process for the namufacture of film of this invention.

Premixed granules of polymers are fed into extruder 1 via hopper 2 and extruded as hot melt film 3 which is fed downwards between the nip of the casting rollers 4 to form the polymer blend film 5. The polymer blend film 5 is fed into stenter 6 where it is stretched to give a voided film. The stenter 6 can be of a type which can be operated in different ways to give the necessary longitudinal and/or transverse stretch. In an alternative process the polymer blend film can be made by blown film extrusion.

The extruded polyurethane and incompatible polymer blend film can be stretched to form the elastomeric film containing voids. The stretching should be carried out at cold draw temperatures for example 10° C.–45° C. preferably at 15° C.–30° C. The stretching can take place in longitudinal or transverse to the extrusion direction. It is preferred that the film is stretched in the transverse direction. It is preferred that the film should be given a stretch of between 200% to 500%. The degree of stretching should be greater than the yield elongation but less than the elongation at break of the film at cold draw temperatures.

After stretching the film is also allowed to contract. These stretching and relaxation stages convert the polyurethane-incompatible blend films into an elastomeric folm containing voids. These voids are normally very small with diameters of between 2 and 12 microns and more usually between 3 and 6 microns.

The dressings of this invention may be prepared from the film of this invention in conventional manner, for example on conventional dressing machines.

EXAMPLE 1

60 parts by weight of Estane 58201 granules and 40 parts by weight of low density polyethylene purge compound from British Petroleum Limited was premixed by tumbling. The mixed granules were fed into a 60 mm Reifenhauser extruder with a length to diameter screw ratio of 20:1 and a compression ratio of 3:1 having a barrel temperature gradient of 165° C. to 185° C. at the die end, and the hot melt polymer blend extruded through a 600 mm slit film die at a rate of 5 meters/min. The molten film was fed between the nip of chill rollers maintained at a temperature of 70° C. and the cooled film wound up. The extruded film was 450 mm wide and 0.0875 mm thick.

The film was given a transverse stretch of 500% and then allowed to contract to 200% of its initial width. The film properties were as follows:

|  | as extruded | after stretching |
|---|---|---|
| Thickness (mm) | 0.0875 | 0.06 |
| Moisture Vapour Transmission rate (g/m²/24 hrs at 37° C. at 100%-10% R.H % difference. | 200 | 643 |

EXAMPLE 2

80 parts by weight of Estane 58201 and 20 parts by weight of high impact polystyrene ref. 6MW from R. H. Cole Ltd. were premixed by tumbling and extruded as Example 1 to form a film 450 mm wide and 0.1 mm thick.
(a) The film was stretched by 500% in the transverse direction and allowed to contract to 200% of its initial width.
(b) The film was stretched by 500% in the lengthwise direction and allowed to contract to 200% of its initial length. The films had the following properties:

|  | as extruded | after stretching a | after stretching b |
|---|---|---|---|
| Thickness (mm) | 0.1 | 0.067 | 0.064 |
| Moisture Vapour Transmission Rate (g/m²/24 hrs at 37° C. at 100%-10% R.H. difference |  | 873 | 773 |

EXAMPLES 3 TO 17

Production of Voided Film

The effect of the processing conditions on the properties of voided films made from polymer blends of polyurethane (PU) reference Estane 58201 and high impact polystyrene (HIPS) reference 6MW (from R. H. Cole Limited) or PU and a low density polyethylene (purge) reference DG 0964 (from B.P. Chemicals Limited) are illustrated by Examples 3 to 17.

The voided films of Examples 3 to 17 were made by extruding a polymer mixture as a hot melt through a flat film die into a cooled two roller casting unit and stretching the resultant film on a laboratory tensometer in the following manner.

Polymer Mixture Preparation (a) Granules of the polyurethane and the incompatible polymer were mixed by tumbling.
(b) The mixture was then fed into a Reifenhauser S60 extruder (melt temperature 190° C., screw speed 38 rpm) and formed into filaments 1 mm to 2 mm in diameter.
(c) The filaments were then cut into 3 mm to 5 mm lengths.
(d) The polymer prepared was then dried in an air circulating oven at 90° C. for 4 hours using 2.5 cm deep trays. (In example 3 steps (b) and (c) were omitted).

Extrusion Conditions

Films were made by feeding the polymer mixture into a 375 mm extruder (Johnson Spartan 150, length to diameter screw ratio of 24:1) and extruding the polymer mixture at a melt temperature of 190° C. through a 300 mm flat film die into the nip of a cooled two roller film casting unit located 7.5 cm directly below the die (rollers maintained at 40° C. and 30° C.).

Stretching Conditions

The voided films were made by stretching samples of the cast films in the machine direction (M) or transverse direction (T) on a laboratory Hounsfield tensometer. The film samples had a gauge length of 50 mm and an aspect ratio of 0.5. Samples were stretched to a draw ratio of 5:1 (400% extension) at rates of between 50 mm/min and 125 mm/min at 20° C. and 25° C. The drawn films were then allowed to contract.

Results

The properties of the thus produced films are given in Table 1. The moisture vapour transmission rate (MVTR) was calculated by the Payne Cup method and the load required to produce 100% strain (Load/100% strain) was calculated from a load/elongation curve derived using samples with a gauge length of 2.54 cm and a width of 2.54 cm measured parallel to the draw direction.

The results show that the MVTR of the voided films is greater than that of films of similar thickness composed of polyurethane alone (cf Estane 58021 MVTR of about 450 g/m²/24 hrs./37° C./100%−10% RH difference for 0.1 mm film). The load/100% strain figures demonstrate that conditions may be varied in order to produce films with various stiffnesses.

TABLE 1

| Example No. | Processing Conditions Die Gap (mm) | Screw Speed (rpm) | Casting Nip Speed (m/min) | Draw Dir$^n$ | Thickness Initial (mm) | Thickness Final (mm) | Final Draw Ratio | Weight of Drawn Film (g/m²) | MVTR (g/m²/24 hr) | Load/100% Strain (kg/2.5cm width) | Composition parts by weight (%) PU | HIPS | Purge |
|---|---|---|---|---|---|---|---|---|---|---|---|---|---|
| 3 | 0.305 | 22.5 | 4.0 | M | 0.102 | 0.046 | 3.04 | 39 | 1079 | 2.93 | 60 | 40 |  |
| 4 | 0.305 | 37.5 | 2.0 | T | 0.305 | 0.229 | 1.92 | 121 | 579 | 1.41 | 60 | 40 |  |
| 5 | 0.305 | 50.0 | 6.0 | T | 0.147 | 0.104 | — | 91 | 574 | 1.35 | 60 | 40 |  |
| 6 | 0.305 | 50.0 | 8.0 | M | 0.106 | 0.041 | 3.20 | 36 | 637 | 4.07 | 60 | 40 |  |
| 7 | 0.153 | 22.5 | 4.0 | T | 0.074 | 0.056 | 1.70 | 51 | 1612 | 0.68 | 60 | 40 |  |
| 8 | 0.305 | 22.5 | 2.0 | M | 0.157 | 0.114 | 2.58 | 46 | 1533 | 1.34 | 50 | 50 |  |
| 9 | 0.153 | 22.5 | 2.0 | M | 0.140 | 0.099 | 2.30 | 87 | 1011 | 2.08 | 60 | 40 |  |
| 10 | 0.153 | 22.5 | 2.0 | T | 0.140 | 0.112 | 1.80 | 99 | 1115 | 1.09 | 60 | 40 |  |
| 11 | 0.153 | 22.5 | 2.0 | M | 0.132 | 0.097 | 2.46 | 75 | 1432 | 2.30 | 50 | 50 |  |
| 12 | 0.153 | 10.0 | 2.0 | M | 0.119 | 0.106 | 2.24 | 49 | 2430 | 0.57 | 50 | — | 50 |
| 13 | 0.153 | 22.5 | 2.0 | T | 0.216 | 0.201 | 2.38 | 92 | 2432 | 0.67 | 50 | — | 50 |
| 14 | 0.153 | 37.5 | 2.0 | T | 0.236 | 2.54 | 175 | 2060 | 1.20 | 50 | — | 50 | |
| 15 | 0.305 | 22.5 | 2.0 | M | 0.152 | 0.135 | 2.30 | — | 3031 | — | 45 | — | 55 |
| 16 | 0.305 | 37.5 | 2.0 | T | 0.234 | 0.208 |  | — | 2367 | — | 45 | — | 55 |

TABLE 1-continued

| Example No. | Processing Conditions | | | | Thickness | | Final Draw Ratio | Weight of Drawn Film (g/m²) | MVTR (g/m²/24 hr) | Load/100% Strain (kg/2.5cm width) | Composition parts by weight (%) | | |
|---|---|---|---|---|---|---|---|---|---|---|---|---|---|
| | Die Gap (mm) | Screw Speed (rpm) | Casting Nip Speed (m/min) | Draw Dir<sup>n</sup> | Initial (mm) | Final (mm) | | | | | PU | HIPS | Purge |
| 17 | 0.305 | 22.5 | 2.0 | T | 0.142 | 0.129 | 1.90 | — | 2072 | — | 50 | — | 50 |

EXAMPLES 18 TO 27

Preparation of Voided Film

Examples 18 to 27 show the effect of varying the draw ratio in machine and transverse directions (including biaxial stretching) on the properties of voided films made from 60/40 polymer blends of polyurethane (PU) reference Estane 58201 and high impact polystyrene (HIPS) reference 6MW from R. H. Cole Limited and 59/40 blends of PU and HIPS also containing 1 part by weight of Brown Pigment reference 15075 from Anstead Limited.

Voided films of Examples 18 to 28 were prepared in a similar manner to that of Examples 3 to 17 except that:
(a) at polymer mixture stage in blends containing a pigment the pigment was predispersed into the polyurethane granules;
(b) at the extrusion stage the films were made by feeding the polymer mixture into a Reifenhauser 560, 60 mm extruder (length to diameter screw ratio of 20:1) and extruding the polymer blend (screw speed 20 rpm) at a melt temperature of 190° C. through a 600 mm flat film die set at a gap of 0.254 mm, into the nip of a cooled two roller (rollers maintained at 40° C. and 30° C.) film casting unit located 13.75 cm directly below the die and rotating at 3.2 meters/min and
(c) at the drawing stage the gauge length of the test samples were 100 mm and the aspect ratios and the draw ratios were varied.

The cast films of Examples 18, 19, 20, 23, 24 and 25 were sequentially drawn in the transverse direction and then in the machine direction. The drawn films were allowed to contract after each draw as in Examples 3 to 17.

Results

The MVTR and load at 100% strain was calculated as in Examples 3 to 17. The tear resistance of the voided films were measured parallel to the final draw direction (by the "Trouser Leg" tear method of ASTM D 1938 using a 0.125 mm slit and a separation speed of 200 mm/minute.

The results set forth in table 2 demonstrate that MVTR of biaxially drawn film increases over that of uniaxially drawn films. The results also demonstrate that biaxially drawn films exhibit an increased tear resistance when compared with films stretched in the machine direction only. (The greatest tear resistance can be obtained by stretching in the transverse direction only; and that transverse stretching may be used to enhance the mechanical orthotropy of the film.

TABLE 2

| Example No. | 1st. Draw | Final Draw Ratio | Aspect Ratio | 2nd. Draw | Final Draw Ratio | Aspect Ratio | Final Thickness (mm) | Final Weight (gsm) | MVTR (g/m²24 hr) | Load/100% strain Width g/2.5 cm (a) | (b) | Tear Resistance (g) | Film Composition |
|---|---|---|---|---|---|---|---|---|---|---|---|---|---|
| 18 | 2:1T | 1.15 | 0.67 | 5:1M | 2.53 | 0.46 | 0.099 | 87 | 829 | 2196 | 721 | 16 ± 1 | 60:40 |
| 19 | 3:1T | 1.40 | " | 5:1M | 2.34 | 0.41 | 0.103 | 84 | 908 | 1960 | 709 | 18.9 | PU:HIPS |
| 20 | 4:1T | 1.70 | " | 5:1M | 2.40 | 0.37 | 0.095 | 73 | 1123 | 1646 | 577 | 17 ± 1 | |
| 21 | 5:1T | — | 0.50 | | | | 0.107 | 91 | 750 | 1263 | 1182 | 144 ± 9 | |
| 22 | 5:1M | — | " | — | — | — | 0.103 | 85 | 661 | 2235 | 603 | 9.3 ± 0.6 | |
| 23 | 2:1T | 1.12 | 0.67 | 5:1M | 2.68 | 0.45 | 0.111 | 95 | 859 | 3163 | 908 | 14.6 ± 1.9 | 50:1:40 PU: |
| 24 | 3:1T | 1.32 | " | 5:1M | 2.68 | 0.38 | 0.104 | 88 | 1096 | 2713 | 712 | 15.5 ± 0.2 | Pigment:HIPS |
| 25 | 4:1T | 1.60 | " | 5:1M | 2.68 | 0.31 | 0.100 | 80 | 1251 | 2285 | 609 | 14.1 ± 0.5 | |
| 26 | 5:1T | 1.86 | 0.50 | | | | 0.126 | 114 | 661 | 1775 | 1425 | 84.7 ± 8.6 | |
| 27 | 5:1M | 2.60 | " | | | | 0.107 | 95 | 827 | 2626 | 854 | 17.0 35 1.9 | |

(a) measured parallel to final draw direction
(b) measured perpendicular to final draw direction

EXAMPLE 28

Preparation of Voided Film

Cast film made by the method of Example 18 was stretched on a tensile test machine (Instron 1195) inside a specially constructed dilatometer. The samples used had a thickness 0.152 mm, a gauge length of 40 mm and an aspect ratio of 0.67. The draw rate was 50 mm/min. at approximately 20° C. maximum extension was 4.75:1. The voided film had a thickness of 0.114 mm at a final (relaxed) draw ratio of 2.05 and a moisture vapour transmission rate of 808 g/m²/24 hours at 37° C. at 100% to 10% relative humidity difference. Dilatometer measurements indicated that the drawn film had increased its volume by 45% at a maximum extension (375%) and by 15% after it had been allowed to relax.

EXAMPLES 29 TO 34

Examples 29 to 34 show the effect of using different thermoplastic polyurethanes in 60/40 blends of polyurethane and high impact polystyrene reference 6MW on the moisture vapour transmitting properties of the voided films.

Voided films of Examples 29 to 34 were prepared in the same manner as Examples 9 or 10.

The MVTR of the voided films were calculated as described in Examples 3 to 17 and are set out in Table 3. These results demonstrate that high MVTR values can be obtained using polyester polyurethanes as well as with polyether polyurethanes.

TABLE 3

| Example No. | Initial Thickness (mm) | Initial Weight (g) | Final Thickness (mm) | Final Weight (g) | MVTR g/m²/ 24 hr. | Composition |
| --- | --- | --- | --- | --- | --- | --- |
| 29 M | 0.175 | 190 | 0.125 | 104 | 1135 | Estane 5714F (A polyether polyurethane) |
| 30 M | 0.158 | 170 | 0.110 | 94 | 1490 | (Pellethane 2103-8AE (A polyether polyurethane) |
| 31 T | 0.158 | 170 | 0.110 | 93 | 1685 | Pellethane 2103-8AE (a polyurethane) |
| 32 M | 0.165 | 174 | 0.113 | 89 | 1460 | Elastollan C85 A10 (A polyester polyurethane) |
| 33 M | 0.190 | 203 | 0.130 | 110 | 1460 | Elastollan P85 A10 (A polyether polyurethane) |
| 34 T | 0.185 | 206 | 0.150 | 121 | 1050 | |

EXAMPLES 35 TO 40

Production of Voided Film

The unpigmented voided films were made by stretching 400 mm wide cast film prepared in the same manner as for Examples 18 to 22 except that in Example 36 the polymer mixture steps (b) and (c) were omitted. The pigmented voided films were made by stretching 400 mm cast film prepared in the same manner as for Examples 23 to 27 except that in Examples 38 and 39 the pigment was dispersed in the high impact polystyrene (HIPS) phase instead of the polyurethane phase (PU).

The voided films of Examples 35 to 50 were prepared by passing the cast films through a Kampf stretcher at ambient room temperature which resulted in the cast films being cold drawn in the machine direction. The cast film used in Example 40 was given a transverse stretch in a stenter before being passed into the Kampf stretcher so that the resulting voided film was drawn biaxially. The films were allowed to contract after each draw.

The results set out in Table 4 were obtained using the methods of Examples 18 to 27 and show larger scale manufacture produces films of similar properties to those of smaller scale manufacture.

The voided films of Examples 35 to 40 were subjected to a hydrostatic pressure test in which a sample film supported a filter paper is subjected to the pressure exerted by a 150 cm column of a water/detergent mixture (contains 1% by weight of Teepol). After 90 minutes no penetration of the films was observed indicating that the films were impermeable to liquid water (cf microporous polyvinylchloride film which at 250 microns fails to support a 80 cm column of aqueous detergent).

TABLE 4

| Example No. | Film Composition % by wt. PU | HIPS | Pigment | Stretching Details | Final Thickness (mm) | Final Weight (g/m²) | MVTR (g/m²/ 24 hr) | Tear (MD) (g) |
| --- | --- | --- | --- | --- | --- | --- | --- | --- |
| 35 | 60 | 40 | — | 5:1 MD | 0.073 | 75 | 1000 | 9.9 |
| 36 | 60 | 40 | — | 5:1 MD | 72 | 570 | 7.7 | |
| 37 | 59 | 40 | 1 | 5:1 MD | 0.08 | 63 | 1130 | 6.0 |
| 38 | 60 | 39 | 1 | 4.75:1 MD | 0.083 | 68 | 790 | 9.4 |
| 39 | 60 | 37.5 | 2.5 | 4.25:1 MD | 0.1 | 90 | 620 | 14.6 |
| 40 | 60 | 40 | — | 3:1 TD, 4:1 MD | 0.1 | 89 | 770 | 21.1 |

EXAMPLES 41 TO 43

Preparation of Adhesive Dressings

Voided films of Examples 35, 47 and 40 were coated with a pressure sensitive adhesive composition consisting of a copolymer of 47 parts by weight of 2-ethyl hexyl acrylate, 47 parts by weight of n-butyl acrylate and 6 parts by weight of acrylic acid polymerised in acetone according to the general method of United Kingdom Application No. 8106707. A dry continuous layer of adhesive at a coating weight of 28 g/m² was obtained.

| Example No. | Film | MVTR (g/m²/24 hr) |
| --- | --- | --- |
| 41 | Ex. 35 | 650 |
| 42 | Ex. 37 | 670 |
| 43 | Ex. 40 | 680 |

The adhesive coated films of Examples 37 and 40 were converted on a standard dressing machine into first aid dressings and Example 35 converted on a standard dressing machine into 7.5 cm×5 cm wound dressings and into larger ward and theatre dressings. The dressings were found to conform well to the skin when applied to the hands of volunteers.

EXAMPLES 44 AND 45

Production of Voided Films

Examples 44 and 45 illustrate the production of voided films from polymer blend films made by a tubular blown film extrusion process.

A polymer mixture of 60 parts by weight of polyurethane (Estane 58201) and 40 parts by weight of high impact polystyrene (reference 6MW from R. H. Cole Limited) was prepared in the same manner as for Examples 3 to 17.

The films were made by feeding the polymer mixture into a Brabender 19 mm 25L/D extruder fitted with a standard polyolefin type screw (4:1 compression ratio) and extruding the polymer mixture (screw speed 120 revs/minute) at a melt temperature of 109° C. through a tubular film die (diameter 2.54 cm, die gap 0.5 mm). The extruded tube was inflated by air pressure to a diameter of 6.5 cm (blow ratio of 2.55:1) or a diameter of 4.0 cm (blow ratio of 1.59:1). Voided films were made by stretching samples of the tubular film to a draw ratio of 5:1 in the transverse direction in the same manner as Examples 3 to 17.

Results

Moisture vapour transmission rates and load at 100% strain of voided films were calculated in the same manner as Examples 3 to 17. The tear resistance of the voided films was measured parallel to the final draw direction as in examples 18 to 27.

The results set forth in Table 5 confirm the results already obtained for the cast flat films of Examples 18 to 27. In particular they confirm that films stretched in the transverse direction only have good tear resistance and are more orthotropic.

TABLE 5

| Example No. | Blow Ratio | Initial Film Thickness (mm) | Final Thickness (mm) | Final Weight (g/m$^2$) | MVTR (g/m$^2$/24 hr.) | Load/100% strain (g/2.5 cm) MD | TD | Tear (MD) (g) |
|---|---|---|---|---|---|---|---|---|
| 44 | 2.55:1 | 0.1 | 0.95 | 55 | 861 | 1440 | 1150 | 160 |
| 45 | 1.59:1 | 0.1575 | 0.13 | 106 | 499 | 1850 | 2070 | 150 |

EXAMPLE 46

Preparation of Voided Films

95 Parts by weight of low density polyethylene (Alkathene 17 from ICI Plastics Limited) and 5 parts by weight of stearamide (Crodamide SR from Croda Chemicals Limited) were uniformly mixed in a shear-mix size 4 (Baker Perkins Limited) at a temperature of 160° C. for 20 minutes. The mixture was discharged into a heated two roller mill (125° C.) and formed into sheet which was subsequently granulated.

A premixture of polyurethane (60 parts by weight of Estane 58201) and the low density polyethylene/stearamide mixture (40 parts by weight) was prepared by tumbling the granules. A cast film was made by hot melt extrusion in the same manner as Example 4 and the voided film made by stretching transverse to the extrusion direction in the same manner as Examples 3 to 17. The stretched film was allowed to contract. The initial film thickness was 0.255 mm, the final film thickness was 0.150 mm and the final film weight per unit area was 101 g/m$^2$.

What is claimed is:

1. A moisture vapour transmitting elastomeric film which does not contain openings or passages which provide a continuous pathway through the film and is impermeable to liquid water comprising a blend of polyurethane and an incompatible polymer wherein the incompatible polymer forms a discrete particulate phase within a continuous matrix of polyurethane and the film contains voids.

2. A moisture vapour transmitting elastomeric film which does not contain openings or passages which provide a continuous pathway through the film and is impermeable to liquid water comprising a blend of polyurethane and a discrete particulate phase wherein the discrete particulate phase comprises an incompatible polymer and the film contains voids.

3. A film according to claim 1 in which the voids have a diameter of 2 microns to 12 microns.

4. A film according to claim 1 in which the film has a moisture vapour transmission rate of at least 350 g/m$^2$/24 hours at 37° C. at 100%—10% relative humidity difference.

5. A film according to claim 1 in which the film has a thickness of 0.0125 mm to 0.125 mm.

6. A film according to claim 1 in which the polyurethane comprises 50% to 80% by weight of the film.

7. A film according to claim 1 in which the incompatible polymer comprises high impact polystyrene.

8. A film according to claim 1 in which the incompatible polymer comprises a low density polyethylene containing inorganic filler.

9. A film according to claim 1 in the form of a medical dressing.

10. A medical dressing according to claim 9 wherein one surface is coated with an adhesive.

11. A film according to claim 1 in which the polyurethane is a linear polyurethane.

12. A film according to claim 11 in which the polyurethane is a linear polyurethane which comprises 45% to 85% of the film by weight.

13. A film according to claim 6 in which the incompatible polymer comprises a vinyl polymer in the form of discrete particles of diameter 2 to 5 microns.

14. A film according to claim 13 in which the vinyl polymer is polystyrene.

15. A film according to claim 13 in which the vinyl polymer is a polyethylene.

16. A medical dressing according to claim 10 in which the adhesive is moisture vapour transmitting and the dressing has a moisture vapour transmission rate of at least 500 g/m$^2$/24 hours at 37° C. at 100% to 10% relative humidity difference.

17. A medical dressing according to claim 10 in which the adhesive is continuous and 12.5 to 75 microns thick.

18. A medical dressing according to claim 17 in which the adhesive comprises an acrylate ester polyer.

19. A film according to claim 1 in which the blend of polyurethane and an incompatible polymer is formed under hot melt conditions.

20. A film according to claim 1 formed by hot melt extrusion.

21. A film according to claim 20 in which the film is stretch oriented in direction transverse to its extrusion direction.

22. A film according to claim 1 in which the film has a recoverable elastic strain of at least 150%.

23. A moisture vapour transmitting elastomeric film from 0.075 mm to 0.125 mm thick which does not contain openings or passages which provide a continuous pathway through the film and is impermeable to liquid water and which comprises a blend of polyurethane and an incompatible polymer in which film the incompatible polymer forms a discrete particulate phase within a continuous matrix of polyurethane and which film contains voids of diameter 2 microns to 12 microns.

24. A film according to claim 23 which contains voids of diameter 3 microns to 6 microns.

25. A film according to claim 23 in which the polyurethane is a linear polyurethane which comprises 45% to 85% of the blend and the incompatible polymer is polyethylene.

26. A film according to claim 23 in which the polyurethane is a linear polyurethane which comprises 45% to 85% of the blend and the incompatible polymer is polystyrene.

27. A film according to claim 26 in which the polystyrene is rubber modified polystyrene.

28. A medical dressing for adhering to skin which comprises a film according to claim 23 and an adhesive on one surface thereon.

29. A film according to claim 24 in the form of a medical dressing.

30. A film according to claim 25 in the form of a medical dressing.

31. A film according to claim 26 in the form of a medical dressing.

32. A film according to claim 27 in the form of a medical dressing.

* * * * *